United States Patent [19]
Metzger et al.

[11] Patent Number: 6,165,223
[45] Date of Patent: Dec. 26, 2000

[54] FLOATING BEARING KNEE JOINT PROSTHESIS WITH A FIXED TIBIAL POST

[75] Inventors: Robert Metzger, Nappanee; David Ray Brown; Troy Hershberger, both of Warsaw; Kevin Cox, Leesburg, all of Ind.

[73] Assignee: Biomet, Inc., Warsaw, Ind.

[21] Appl. No.: 09/259,873

[22] Filed: Mar. 1, 1999

[51] Int. Cl.[7] .................................................. A61F 2/38
[52] U.S. Cl. ................................. 623/20.27; 623/20.14; 623/20.24
[58] Field of Search .................................. 623/20, 18, 16

[56] References Cited

U.S. PATENT DOCUMENTS

| | | |
|---|---|---|
| 3,728,742 | 4/1973 | Averill et al. . |
| 3,748,662 | 7/1973 | Helfet . |
| 3,774,244 | 11/1973 | Walker . |
| 3,958,278 | 5/1976 | Lee et al. . |
| 3,964,106 | 6/1976 | Hutter, Jr. et al. . |
| 3,996,624 | 12/1976 | Noiles . |
| 4,081,866 | 4/1978 | Upshaw et al. . |
| 4,085,466 | 4/1978 | Goodfellow et al. . |
| 4,094,017 | 6/1978 | Matthews et al. . |
| 4,136,405 | 1/1979 | Pastrick et al. . |
| 4,207,627 | 6/1980 | Cloutier . |
| 4,209,861 | 7/1980 | Walker et al. . |

(List continued on next page.)

FOREIGN PATENT DOCUMENTS

| | | |
|---|---|---|
| 0 186 471 A3 | 7/1986 | European Pat. Off. . |
| 0 327 297 A2 | 2/1988 | European Pat. Off. . |
| 0 381 352 A1 | 1/1989 | European Pat. Off. . |
| 0 346 183 A1 | 12/1989 | European Pat. Off. . |
| 0 349 173 A1 | 1/1990 | European Pat. Off. . |
| 0 442 330 A2 | 2/1991 | European Pat. Off. . |
| 0 498 586 A1 | 2/1991 | European Pat. Off. . |
| 0 510 299 A1 | 4/1991 | European Pat. Off. . |
| 0 510 178 B1 | 10/1992 | European Pat. Off. . |
| 0 627 203 A2 | 12/1994 | European Pat. Off. . |
| 3529 894 A1 | 3/1987 | Germany . |
| 4009 360 A1 | 8/1991 | Germany . |
| 1 534 263 | 11/1978 | United Kingdom . |
| 2 219 942 | 12/1989 | United Kingdom . |
| 2 296 443 | 7/1996 | United Kingdom . |
| WO 92/03108 | 3/1992 | WIPO . |
| WO 92/08424 | 12/1992 | WIPO . |
| WO 94/26212 | 11/1994 | WIPO . |
| WO 96/03097 | 2/1996 | WIPO . |
| WO 96/24311 | 8/1996 | WIPO . |
| WO 98/02116 | 1/1998 | WIPO . |

OTHER PUBLICATIONS

"AGC, Total Knee System, Tradition Series", brochure, Biomet, Inc., copyright 1995.
"Interaction Between Active And Passive Knee Stabilizers During Level Walking", O.D. Schipplein and T.P. Andriacchi, Journal of Orthopaedic Research, 1991.
"Maxim, The Complete Knee System" brochure, Biomet, Inc., copyright 1995.

(List continued on next page.)

*Primary Examiner*—Paul J. Hirsch
*Assistant Examiner*—Michael B. Priddy
*Attorney, Agent, or Firm*—Harness, Dickey & Pierce P.L.C.

[57] ABSTRACT

The invention relates to a floating bearing knee joint prosthesis having a fixed tibial post used for replacing the articulating knee portion of a femur and a tibia. The floating bearing knee joint prosthesis includes a femoral component, a tibial component, a bearing member and a guide post. The femoral component includes an engagement member, a first femoral bearing surface and a second femoral bearing surface. The tibial component includes a tibial bearing surface. The bearing member includes a first bearing surface which is operable to articulate with the first femoral bearing surface, a second bearing surface which is operable to articulate with the second femoral bearing surface and a third bearing surface which is operable to articulate with the tibial bearing surface. The guide post extends from the tibial component and is operable to be engaged by the engagement member of the femoral component such that upon engagement, the femoral component forces the bearing member to move posteriorly relative to the tibial component.

20 Claims, 5 Drawing Sheets

U.S. PATENT DOCUMENTS

| | | |
|---|---|---|
| 4,213,209 | 7/1980 | Insall et al. . |
| 4,215,439 | 8/1980 | Gold et al. . |
| 4,216,549 | 8/1980 | Hillberry et al. . |
| 4,219,893 | 9/1980 | Noiles . |
| 4,224,696 | 9/1980 | Murray et al. . |
| 4,224,697 | 9/1980 | Murray et al. . |
| 4,257,129 | 3/1981 | Volz ......................................... 623/20 |
| 4,285,070 | 8/1981 | Averill . |
| 4,298,992 | 11/1981 | Burstein et al. . |
| 4,301,553 | 11/1981 | Noiles . |
| 4,309,778 | 1/1982 | Buechel et al. . |
| 4,340,978 | 7/1982 | Buechel et al. . |
| 4,462,120 | 7/1984 | Rambert et al. .......................... 623/20 |
| 4,470,158 | 9/1984 | Pappas et al. . |
| 4,538,305 | 9/1985 | Engelbrecht et al. . |
| 4,568,348 | 2/1986 | Johnson et al. . |
| 4,586,933 | 5/1986 | Shoji et al. . |
| 4,634,444 | 1/1987 | Noiles . |
| 4,637,382 | 1/1987 | Walker . |
| 4,673,407 | 6/1987 | Martin . |
| 4,711,639 | 12/1987 | Grundei . |
| 4,714,474 | 12/1987 | Brooks, Jr. et al. . |
| 4,728,332 | 3/1988 | Albrektsson . |
| 4,808,185 | 2/1989 | Penenberg et al. . |
| 4,822,362 | 4/1989 | Walker et al. . |
| 4,822,365 | 4/1989 | Walker et al. . |
| 4,865,607 | 9/1989 | Witzel et al. . |
| 4,883,488 | 11/1989 | Bloebaum et al. . |
| 4,888,021 | 12/1989 | Forte et al. . |
| 4,892,547 | 1/1990 | Brown . |
| 4,911,721 | 3/1990 | Branemark et al. . |
| 4,950,297 | 8/1990 | Elloy et al. . |
| 4,950,298 | 8/1990 | Gustilo et al. ............................ 623/20 |
| 4,959,071 | 9/1990 | Brown et al. . |
| 5,007,933 | 4/1991 | Sidebotham et al. ..................... 623/20 |
| 5,011,496 | 4/1991 | Forte et al. . |
| 5,037,439 | 8/1991 | Albrektsson et al. . |
| 5,047,057 | 9/1991 | Lawes . |
| 5,064,437 | 11/1991 | Stock et al. . |
| 5,071,438 | 12/1991 | Jones et al. . |
| 5,080,675 | 1/1992 | Lawes et al. . |
| 5,092,895 | 3/1992 | Albrektsson et al. . |
| 5,116,375 | 5/1992 | Hofmann . |
| 5,116,376 | 5/1992 | May . |
| 5,133,758 | 7/1992 | Hollister . |
| 5,147,405 | 9/1992 | Van Zile et al. . |
| 5,171,283 | 12/1992 | Pappas et al. . |
| 5,176,710 | 1/1993 | Hahn et al. . |
| 5,197,987 | 3/1993 | Koch et al. . |
| 5,219,362 | 6/1993 | Tuke et al. ................................ 623/20 |
| 5,226,916 | 7/1993 | Goodfellow et al. . |
| 5,271,747 | 12/1993 | Wagner et al. . |
| 5,282,868 | 2/1994 | Bahler . |
| 5,282,870 | 2/1994 | Moser et al. . |
| 5,314,482 | 5/1994 | Goodfellow et al. . |
| 5,314,483 | 5/1994 | Wehrli et al. . |
| 5,330,533 | 7/1994 | Walker . |
| 5,330,534 | 7/1994 | Herrington et al. . |
| 5,358,527 | 10/1994 | Forte . |
| 5,358,530 | 10/1994 | Hodorek . |
| 5,358,531 | 10/1994 | Goodfellow et al. . |
| 5,370,699 | 12/1994 | Hood et al. . |
| 5,370,700 | 12/1994 | Sarkisian et al. . |
| 5,370,701 | 12/1994 | Finn . |
| 5,387,240 | 2/1995 | Pottenger et al. . |
| 5,395,401 | 3/1995 | Bahler . |
| 5,413,604 | 5/1995 | Hodge . |
| 5,413,608 | 5/1995 | Keller . |
| 5,480,446 | 1/1996 | Goodfellow et al. . |
| 5,514,183 | 5/1996 | Epstein et al. . |
| 5,549,686 | 8/1996 | Johnson et al. . |
| 5,549,689 | 8/1996 | Epstein et al. . |
| 5,556,432 | 9/1996 | Kubein-Meesenburg et al. . |
| 5,571,197 | 11/1996 | Insall . |
| 5,609,639 | 3/1997 | Walker . |
| 5,609,643 | 3/1997 | Colleran et al. .......................... 623/20 |
| 5,609,645 | 3/1997 | Vinciguerra ............................... 623/20 |
| 5,658,342 | 8/1997 | Draganich et al. . |
| 5,658,344 | 8/1997 | Hurlburt . |
| 5,683,467 | 11/1997 | Pappas . |
| 5,683,468 | 11/1997 | Pappas . |
| 5,702,458 | 12/1997 | Burstein et al. . |
| 5,702,466 | 12/1997 | Pappas et al. . |
| 5,725,584 | 3/1998 | Walker et al. . |
| 5,755,801 | 5/1998 | Walker et al. . |
| 5,755,802 | 5/1998 | Gerber . |
| 5,824,102 | 10/1998 | Buscayret ................................. 623/20 |
| 5,824,103 | 10/1998 | Williams .................................. 623/20 |
| 5,871,542 | 2/1999 | Goodfellow et al. . |
| 5,871,545 | 2/1999 | Goodfellow et al. ..................... 623/20 |
| 5,871,546 | 2/1999 | Colleran et al. .......................... 623/20 |
| 5,879,392 | 3/1999 | McMinn . |
| 5,906,643 | 5/1999 | Walker . |
| 5,906,943 | 5/1999 | Walker . |

OTHER PUBLICATIONS

"Performance, The Total Knee System", brochure, Biomet, Inc., copyright 1997.

"The Role of Joint Load in Knee Stability", Keith L. Markolf, PhD, William L. Bargar, M.D., Stephen C. Shoemaker, B.S. and Harlan C. Amstutz, M.D., Journal of Bone and Joine Surgery, Incorporated, copyright 1981.

"Trac Knee System" Design Rationale, Louis F. Draganich, PhD, Lawrency A. Pottenger, M.D., PhD., Nov. 1996.

Aglietti, P., Buzzi, R., and Menchetti, P.P.M., "Total Knee Replacement—Problems Related to the Posterior Cruciate Ligament and Fixed Versus Mobile Bearings," European Federation of National Associations of Orthopaedics and Traumatology, pp. 15–24, undated (1996 or later).

H. Kurosawa, et al., "Geometry And Motion Of The Knee For Implant And Orthotic Design," J. Biomechanics, vol. 18, No. 7, pp. 287–499 (1985).

Menchetti, Paolo, M., M.D.; Walker, Peter, S. PhD, "Mechanical Evaluation of Mobile Bearing Knees," The American Journal of Knee Surgery, vol. 10, No. 2, Spring 1997, pp. 73–82.

FLOATING BEARING KNEE JOINT PROSTHESIS WITH A FIXED TIBIAL POST

BACKGROUND OF THE INVENTION

1. Field of the Invention

This invention relates generally to a knee joint prosthesis which replaces the articulating knee portion of the femur and tibia, and more particularly, to a floating bearing knee joint prosthesis having a fixed tibial post.

2. Discussion of the Related Art

A knee joint prosthesis typically comprises a femoral component and a tibial component. The femoral component and the tibial component are designed to be surgically attached to the distal end of the femur and the proximal end of the tibia, respectively. The femoral component is further designed to cooperate with the tibial component in simulating and articulating motion of an anatomical knee joint.

Motion of a natural knee is kinematically complex. During a relatively broad range of flexion and extension, the articular or bearing surfaces of a natural knee experience rotation, medial and lateral angulation, translation in the sagittal plane, rollback and sliding. Knee joint prostheses, in combination with ligaments and muscles, attempt to duplicate this natural knee motion, as well as absorb and control forces generated during the range of flexion. Depending on the degree of damage or deterioration of the knee tendons and ligaments, however, it may be necessary for a knee joint prosthesis to eliminate one or more of these motions in order to provide adequate stability.

While knee joint prostheses are effective in replacing the anatomical knee joint, they nevertheless follow different design options that each have different advantages and disadvantages. For example, many knee joint prostheses are polycentric, such that the posterior femoral radius is smaller than the distal femoral radius. The reason for the change in radius is to provide an appropriately sized femoral component, facilitate early rollback, and to allow for full flexion. However, because of the smaller posterior femoral radius, such knee joint prostheses provide a large articulating contact area in extension, but as the knee joint prosthesis moves during flexion, the smaller posterior radius creates a smaller articulating contact area as flexion increases. This generally reduces the contact area from a large surface contact area to a smaller contact area between the femoral component and the tibial component. For example, the contact area may be about 275 mm$^2$ at extension and reduce substantially to about 75 mm$^2$ at 60° to 90° of flexion. This reduced contact area may not be optimal for long term durability due to increased contact stresses.

Other knee joint prostheses attempt to eliminate this disadvantage by using a roller and trough articulation, where the roller and trough are spherically or cylinderally shaped to provide full contact area throughout the range of motion from extension to flexion. However, the disadvantage with most of these type knee joint prostheses is that posterior rollback of the femoral component relative to the tibial component is eliminated. Such rollback is extremely desirable because it increases the extension moment arm, increases quadriceps efficiency, and helps patients perform activities of daily living, such as climbing stairs. In addition, these types of designs are typically rotationally constrained.

Other knee joint prostheses attempt to eliminate the above disadvantages using another design option, such as a meniscus or floating bearing between the femoral component and the tibial component. By utilizing a floating bearing, the articulating contact area between the femoral component and the bearing can theoretically be increased without increasing constraint. However, some of the knee joint prostheses that provide a floating bearing rely on ligaments for femoral rollback which in many cases may not be reliable.

Knee joint prostheses are also generally provided having different levels of constraint. For example, primary type knee joint prostheses provide the least level of constraint, posterior stabilized (PS) knee joint prostheses provide an intermediate level of constraint, while fully constrained type knee joint prostheses provide the highest level of constraint upon the kinematic motions of a knee joint. In some situations, a patient may initially have a less constrained type knee joint implanted, such as a primary or posterior stabilized (PS) knee joint prosthesis. Should the patient later require a fully constrained type knee joint prosthesis because the patient is exhibiting instability, a surgeon is generally required to remove the entire knee joint prosthesis and implant both a new femoral and tibial component or a new fixed bearing to provide a fully constrained knee joint prosthesis. However, such extensive surgical modifications increases the overall surgical cost and complexity of upgrading a knee joint prosthesis from one constraint to another.

What is needed then is a knee joint prosthesis which does not suffer from the above mentioned disadvantages. This in turn, will provide a substantially conforming contact area between the articulating surfaces of the femoral component and the tibial component throughout extension and flexion, increase and provide a substantially constant articulating contact surface area from extension through flexion, reduce overall stresses and wear in the articulating contact area, provide femoral rollback relative to the tibial component by means of a floating bearing, provide a mechanical engagement mechanism to force femoral rollback without having to rely on soft tissue ligaments, increase the overall reliability of the knee joint prosthesis, prevent anterior movement of the bearing and provide a modular knee joint prosthesis that can achieve different levels of constraint by simply replacing a guide post that is fixed to the tibial component. It is, therefore, an object of the present invention to provide a floating or rotating bearing knee joint prosthesis with a fixed tibial post that achieves the above-identified advantages.

SUMMARY OF THE INVENTION

In accordance with the teachings of the present invention, a floating or rotating bearing knee joint prosthesis with a fixed tibial post for use in replacing the articulating knee portion of a femur and a tibia is disclosed. The floating bearing knee joint prosthesis with the fixed tibial post provides a substantially full or large contact surface between a femoral component, a tibial component and a bearing member from full extension to full flexion with the contact surface between the condyles of the femoral component and the bearing member being greater than about 300 mm$^2$ from extension to full flexion.

In one preferred embodiment, a knee joint prosthesis for replacing the articulating knee portion of a femur and a tibia includes a femoral component, a tibial component, a bearing member and a guide post. The femoral component includes an engagement member, a first femoral bearing surface and a second femoral bearing surface. The tibial component includes a tibial bearing surface. The bearing member includes a first bearing surface which is operable to articulate with the first femoral bearing surface, a second bearing surface which is operable to articulate with the second femoral bearing surface and a third bearing surface which is operable to articulate with the tibial bearing surface. The guide post extends from the tibial component and is operable to be engaged by the engagement member of the femoral component.

In another preferred embodiment, a knee joint prosthesis for replacing the articulating knee portion of a femur and a tibia includes a femoral component, a tibial component, a bearing member and a removable guide post. The femoral component includes at least one femoral bearing surface and the tibial component includes at least one tibial bearing surface. The bearing member includes a first bearing surface which is operable to articulate with the at least one femoral bearing surface and a second bearing surface which is operable to articulate with the at least one tibial bearing surface. The removable guide post is removably coupled to the tibial component and is operable to be engaged by the femoral component such that upon engagement, the femoral component controls at least a portion of the movement of the bearing member relative to the tibial component.

In yet another preferred embodiment, a knee joint prosthesis system for replacing the articulating knee portion of a femur and a tibia includes a first femoral component, a second femoral component, a tibial component, a bearing member and a plurality of removable guide posts. The first femoral component includes at least a first femoral bearing surface and the second femoral component includes at least a second femoral bearing surface. The tibial component includes at least one tibial bearing surface. The bearing member includes a first bearing surface which is operable to articulate with one of the first and second femoral bearing surfaces and a second bearing surface operable to articulate with said at least one tibial bearing surface. Each of the removable guide posts are operable to be removably coupled to the tibial component such that selection of one of the removable guide posts and one of the femoral components changes the type of constraint exhibited by the femoral knee joint prosthesis system.

The use of the present invention provides a floating bearing knee joint prosthesis with a fixed tibial post. The floating bearing knee joint prosthesis provides a substantially full contact surface between its components from full extension to full flexion. As a result, the aforementioned disadvantages associated with the currently available knee joint prostheses have been substantially reduced or eliminated.

BRIEF DESCRIPTION OF THE DRAWINGS

Still other advantages of the present invention will become apparent to those skilled in the art after reading the following specification and by reference to the drawings in which.

DETAILED DESCRIPTION OF THE PREFERRED EMBODIMENT(S)

The following description of the preferred embodiments concerning a floating bearing knee joint prosthesis with a fixed modular tibial post are merely exemplary in nature and are not intended to limit the invention or its application or uses. Moreover, while the present invention is described in detail below generally with respect to a posterior stabilized (PS) knee joint prosthesis, it will be appreciated by those skilled in the art that the present invention is clearly not limited to only a posterior stabilized (PS) knee joint prosthesis and may be applied to various other types of knee joint prosthesis such as a primary knee joint prosthesis and a fully constrained knee joint prosthesis, as further discussed herein.

Figures 1, 2, 3:
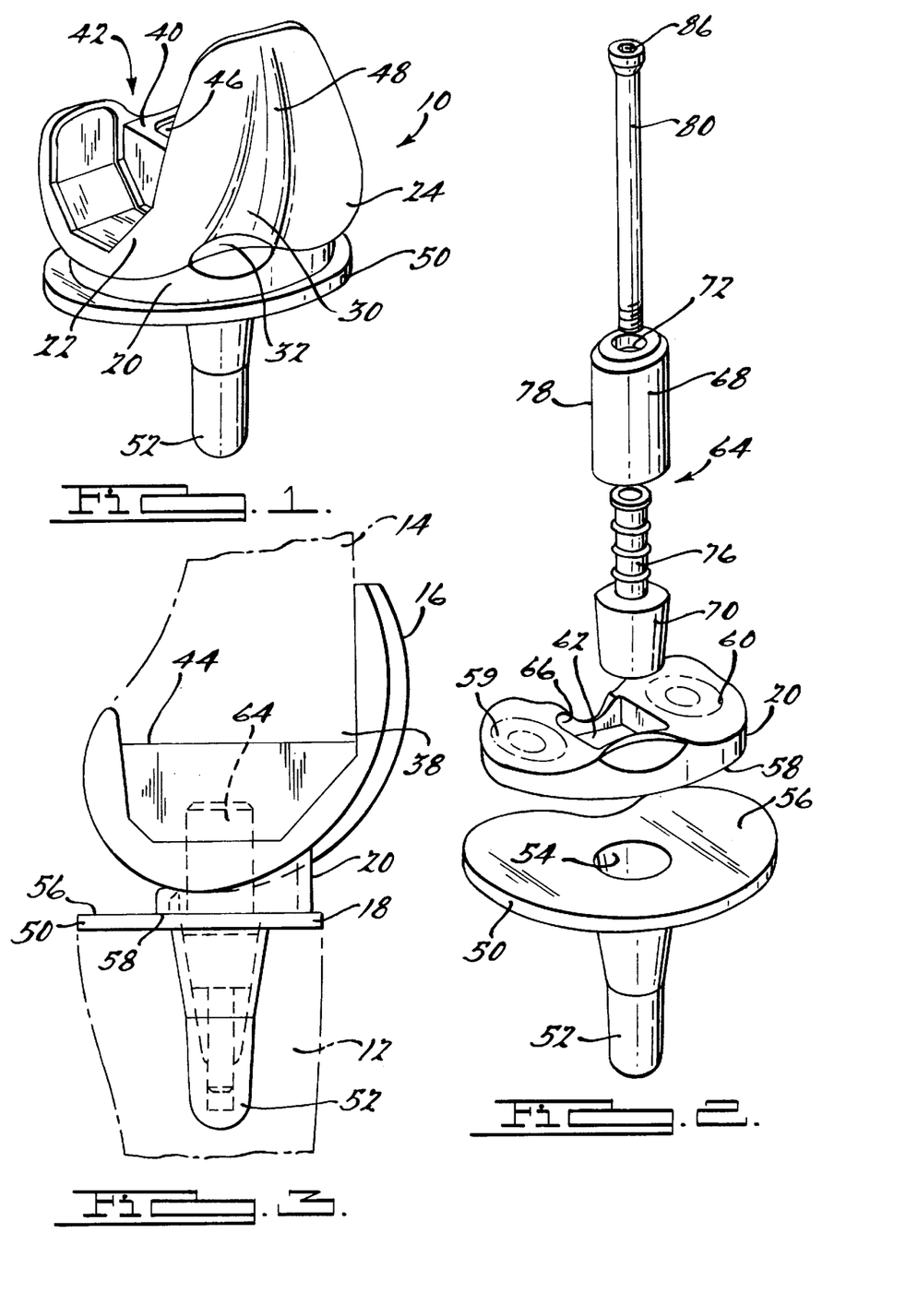
FIG. 1 is a perspective view of a posterior stabilized (PS) knee joint prosthesis according to the teachings of a first preferred embodiment of the present invention.
FIG. 2 is an exploded perspective view of a tibial component and bearing element of the posterior stabilized (PS) knee joint prosthesis of FIG. 1.
FIG. 3 is a sagittal elevational view of the posterior stabilized (PS) knee joint prosthesis shown in FIG. 1 with a tibia and a femur of the natural knee shown in phantom.
Figures 4, 5A, 5B:
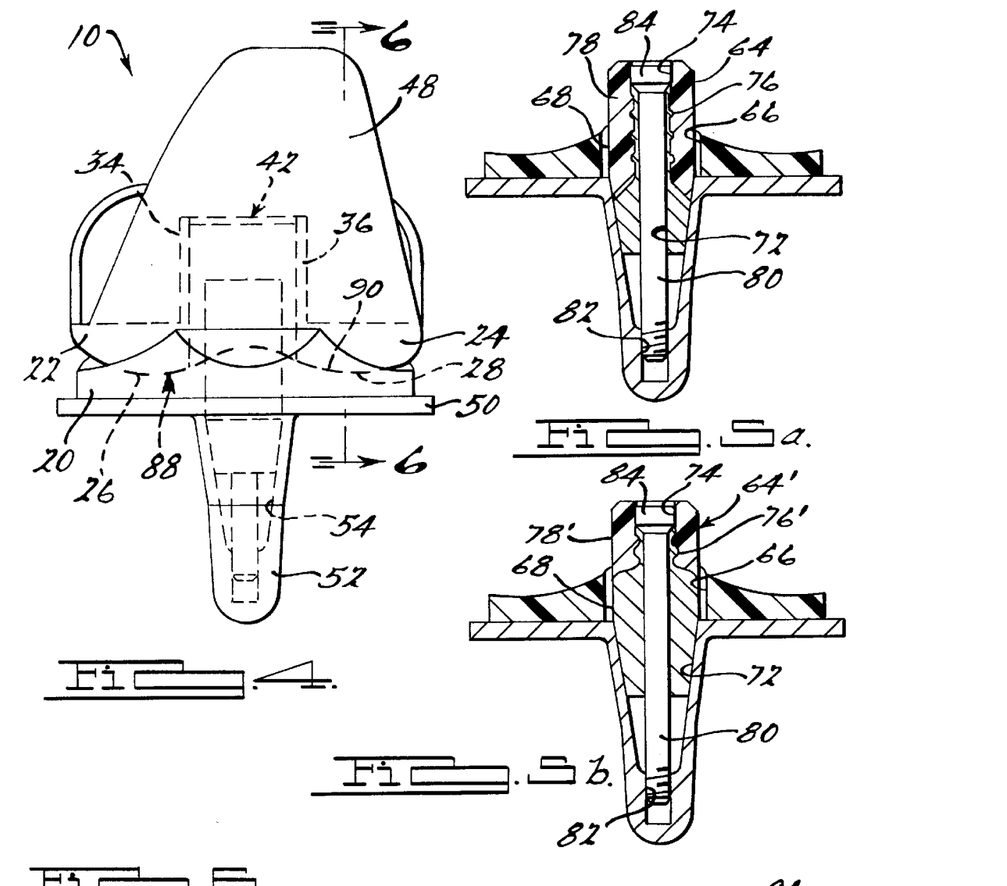
FIG. 4 is a coronal elevational view of the posterior stabilized (PS) knee joint prosthesis shown in FIG. 1 with the tibia and the femur of the natural knee shown in phantom.
FIG. 5a is a coronal sectional view of the tibial component and bearing member of the posterior stabilized (PS) knee joint prosthesis of FIG. 3.
FIG. 5b is a coronal sectional view of the tibial component and bearing member of the posterior stabilized (PS) knee joint prosthesis of FIG. 3 according to the teaching of a second preferred embodiment of the present invention.

Referring to FIGS. 1–4, there is shown a knee joint prosthesis 10 according to the teachings of a first preferred embodiment of the present invention. The knee joint prosthesis 10 is generally known as a posterior stabilized (PS) knee joint prosthesis 10 which is designed to provide adequate stability in case of moderate deterioration or instability of the human knee. This most typically occurs when the anterior and posterior cruciate ligaments are sacrificed or dysfunctional and the medial and lateral collateral ligaments remain functionally intact. The knee joint prosthesis 10 is shown in FIGS. 3 and 4 as being secured to a tibia 12 and a femur 14 of a surgically resected left knee joint, with the tibia 12 and the femur 14 shown in phantom, and with the understanding that a suitable right knee joint prosthesis can be similarly constructed. The knee joint prosthesis 10 includes a femoral component 16, a tibial component 18 and a floating tibial bearing 20.

The femoral component 16 is adapted to be secured to a distal end of the femur 14 and includes a first condylar portion 22 and a second condylar portion 24 that provide a first femoral bearing surface 26 and a second femoral bearing surface 28, respectively. The first and second condylar portions 22 and 24 of the femoral component 16 are interconnected by an intercondylar portion 30 that defines an intercondylar recess 32. The intercondylar portion 30 includes a first lateral sidewall 34 and a second lateral sidewall 36 that are substantially planar and parallel to one another. The anterior portions of the first and second lateral sidewalls 34 and 36 are connected by an anterior wall 38 and the posterior portions of the first and second lateral sidewalls 34 and 36 are connected by a posterior engagement member or elongated cam 40. The intercondylar portion 30 which includes the first and second lateral sidewalls 34 and 36, the anterior wall 38 and the posterior engagement member 40 define the perimeter of a box 42 that defines the intercondylar recess 32.

Positioned atop the box 42 is a substantially planar integral top 44 that defines an elongated opening or bore 46. A closed box may also be utilized in place of the open box 42. The femoral component 16 further includes an arcuate patellar portion 48 which is disposed on the anterior surface of the femoral component 16. The patellar portion 48 is shaped to allow anatomical tracking of a natural or prosthetic patella. The patella prostheses which are compatible with the present invention may be of varying shape, such as round or dome shaped and may be constructed from polyethylene, polyethylene with metal backing or other suitable materials. The femoral component 16 including the box 42 is preferably formed as a unitary structure and preferably cast of a biocompatible high strength alloy, such as a cobalt—chromium—molybdenum alloy or other suitable material. All surfaces which do not contact the femur 14 are preferably highly polished to provide smooth articulating bearing surfaces.

The tibial component 18 is adapted to be secured to the proximal end of the tibia 12 after the tibia has been resected in a manner known in the art. The tibial component 18 includes a substantially planar platform-like tibial tray 50 and an inferiorly extending tibial stem 52. The tibial stem 52 is adapted to be received in a corresponding opening made by the surgeon in the longitudinal center of the tibia 12. The tibial tray 50 and the tibial stem 52 define a conically shaped bore 54 axially extending through the tibial tray 50 and into the stem 52. The tibial tray or plateau 50 and stem 52 are preferably manufactured from cobalt—chromium—molybdenum or any other suitable biocompatible material. The top of the tibial tray 50 is highly polished to provide a substantially smooth tibial bearing surface 56.

The floating or rotating bearing 20 is located between the femoral component 16 and the tibial component 18. The floating bearing 20 has a substantially planar inferior bearing surface 58 which slidably moves relative to the highly polished tibial bearing surface 56, further discussed herein. The floating bearing 20 further includes a first superior articulating or bearing surface 59 and a second superior articulating or bearing surface 60. The first bearing surface 59 and the second bearing surface 60 articulate with the first bearing surface 26 of the condyle 22 and the second bearing surface 28 of the condyle 24 of the femoral component 16. Positioned between the first and second bearing surfaces 59 and 60 is a substantially rectangular opening 62 that is slidably positioned about a center modular guide post 64. The opening 62 is defined by a substantially perpendicular peripheral sidewall 66 which is operable to engage the center guide post 64. The floating bearing 20 is preferably formed from a surgical grade, low friction, low wearing plastic, such as UHMWPE or other suitable material.

The center guide post 64 includes a substantially oval shaped outer peripheral sidewall 68 or any other appropriately shaped sidewall and a conically tapered sidewall 70. The conically tapered sidewall 70 is operable to be nestingly received within the conically tapered bore 54 to provide a friction fit that forms a Morse-type taper. Alternatively, the center guide post 64 may be formed integral with the tibial component 18. Extending axially through the center guide post 64 is a substantially cylindrical bore 72 having a superiorly located counterbore 74, as shown clearly in FIG. 5a. The center guide post 64 is formed from a combination of a cobalt—chromium—molybdenum portion 76 and a molded polymer portion 78 formed from UHMWPE or other suitable material. The polymer portion 78 extends to the base of the tibial tray 50 to provide a polymer/polymer contact between the centering post 64 and the floating bearing 20, via sidewalls 66 and 68.

Axially extending through the bore 72 is a threaded bolt 80 which threadably engages a threaded bore 82 located inferiorly of the stem 52. The bolt 80 further includes a head 84 which is nestingly received within counterbore 74. The head 84 includes a hexagonal drive 86 that may be rotatably engaged by a hexagonal drive member. Upon threadably engaging bolt 80 within bore 82, the centering post 64 is rigidly secured, via the Morse-type taper formed from the conical bore 54 and the conical sidewall 70.

Referring to FIG. 5b, a second embodiment of a centering post 64' is shown. In this regard, like reference numerals will be used to identify like structures with respect to the centering post 64. The centering post 64' is substantially similar to the centering post 64 except that the metal portion 76' extends above the tibial tray 50, thereby providing a reduced or smaller polymer portion 78'. In this configuration, a polymer/metal contact or interface is formed between the floating bearing 20 and the centering post 64', via the sidewalls 66 and 68.

Figure 6:
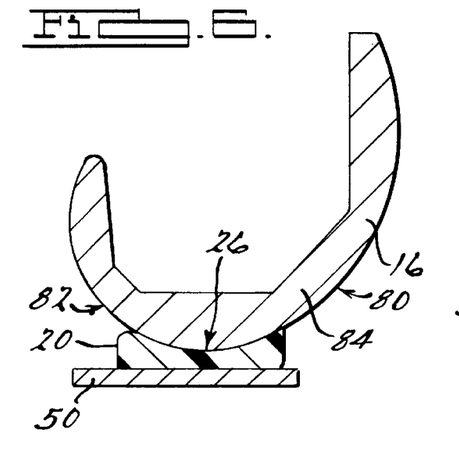
FIG. 6 is a sagittal sectional view of the posterior stabilized (PS) knee joint prosthesis taken through line 6—6 of FIG. 4.

Turning to FIGS. 4 and 6, the articulating bearing surfaces 26 and 28 of the first and second condyles 22 and 24 of the femoral component 16 are shown cooperating with the bearing surfaces 59 and 60 of the floating bearing 20. In this regard, each condyle 22 and 24 of the femoral component 16 has a polycentric bearing surface 26 and 28, respectively along the sagittal plane. In other words, each bearing surface 26 and 28 is defined by a large anterior radius 80 and a smaller posterior/distal radius 82. The large anterior radius 80 is preferably about 1.497 inches and extends to about point 84. The posterior/distal radius 82 is about 0.945 inches and extends anterior the center line of the femoral component 16 up to point 84. Point 84 is located just anterior the floating bearing 20. Correspondingly, the bearing surface 59 and 60 of the floating bearing 20 are formed with a single radius 86 along the sagittal plane having a radius of about 0.945 inches. Because the sagittal posterior/distal radius 82 of the femoral component 16 extends beyond the axial center line of the femoral component 16 anteriorly to point 84, this radius congruently mates with the radius 86 of the floating bearing 20 from extension to full flexion. This mating provides a substantially fully mated and constant contact surface area between the femoral component 16 and the floating bearing 20 substantially through extension and flexion along the sagittal plane.

Each bearing surface 26 and 28 of the condyles 22 and 24 are arcuately shaped with a constant radius 88 of about 1.6 inches along the coronal plane. Correspondently, the bearing surfaces 59 and 60 of the floating bearing 20 are likewise, formed from a constant radius 90 of about 1.6 inches along the coronal plane. Each of the radii 88 and 90 congruently mate with one another to provide substantially full surface contact along the coronal plane from extension to flexion. This full surface contact along both the sagittal and coronal planes substantially evenly disburses stresses between the femoral component 16 and the floating bearing 20, as opposed to femoral components, which merely provide a smaller contact area, such as a line or point contact, either along the sagittal plane or the coronal plane which focuses stresses at these contact points, thereby potentially increasing wear in these areas. In other words, a contact area of greater than about 300 mm$^2$ is maintained from extension to full flexion between the femoral component 16 and the floating bearing 20.

Figure 7:
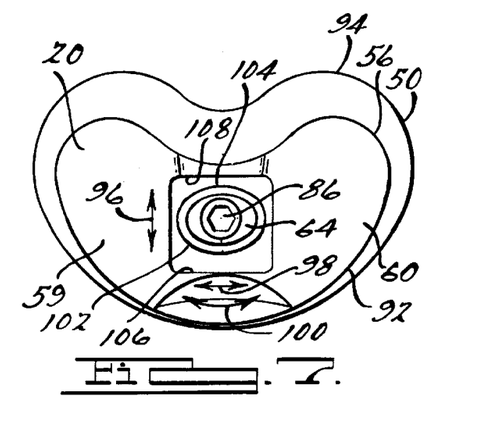
FIG. 7 is a top view of the assembled tibial component and bearing member of FIG. 1.

Referring now to FIG. 7, a top view of the assembled tibial component 18, along with the floating bearing 20 is shown. In this regard, the floating bearing 20 has an outer peripheral wall 92 which is substantially concentric with the outer peripheral wall 94 of the tibial tray 50. With the floating bearing 20 positioned atop the tibial tray 50 in extension, the guide post 64 is positioned just posteriorly the opening 62 defined by sidewall 66. It should be noted that the post 64 is sized relative to the opening 62 such that the posterior stabilized knee joint prosthesis 10 provides anterior and posterior movement 96, medial to lateral movement 98, and rotation movement 100 of the floating bearing 20 relative to the tibial component 18. Moreover, the femoral component 16 provides rotational movement along the sagittal plane relative to the floating bearing 20, as well as varus and valgus movement relative to the floating bearing 20. The posterior stabilized knee joint prosthesis 10 may also simply provide the anterior to posterior movement 96 and the rotational movement 100 and eliminate the medial to lateral movement 98 of the floating bearing 20 relative to the tibial tray 50.

Figures 8A, 8B, 8C, 8D:
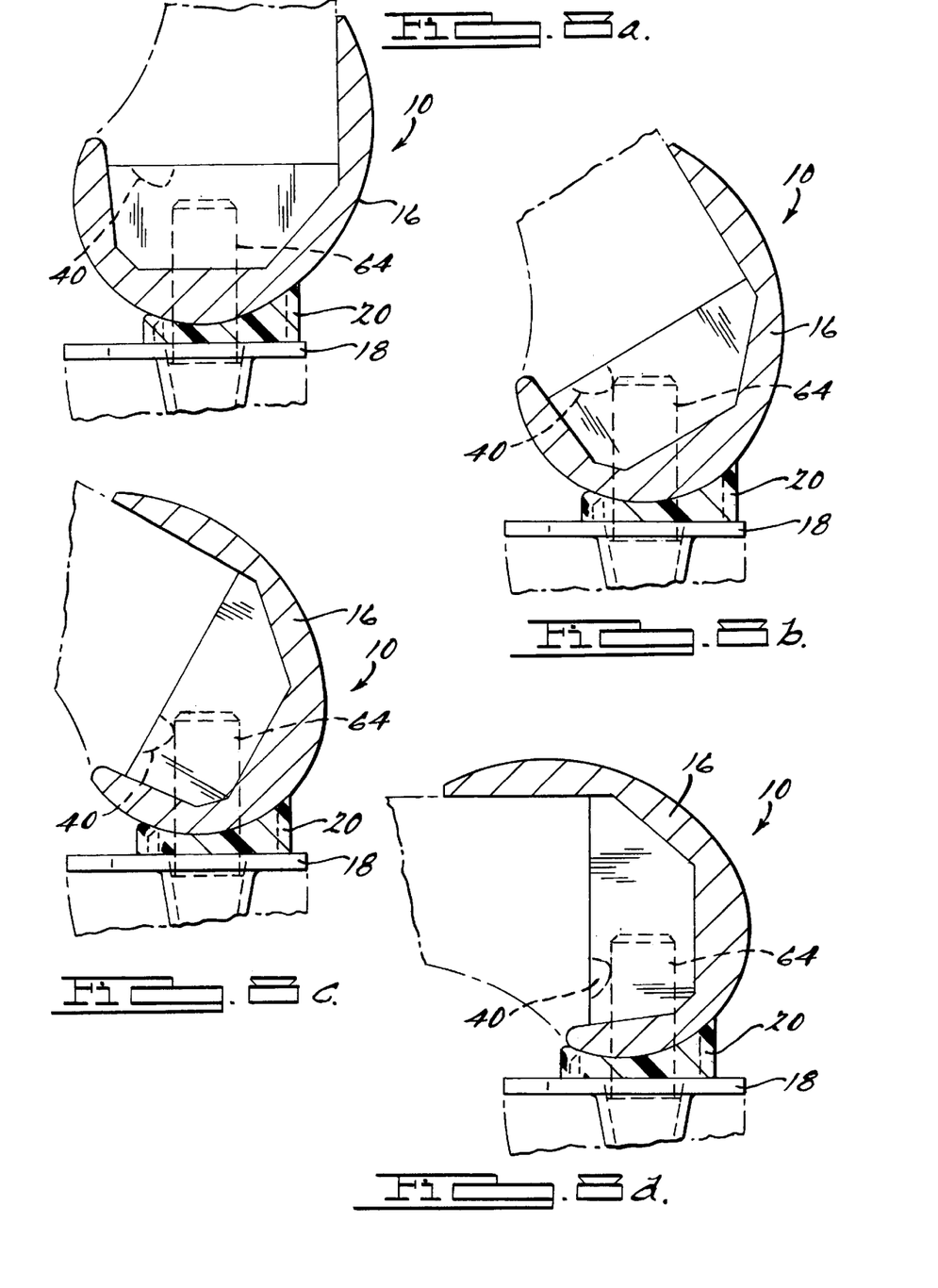
FIGS. 8a–8e are partial sagittal sectional views of the posterior stabilized (PS) knee joint prosthesis shown in FIG. 1 illustrating five different positions of the femoral component with respect to the tibial component during a range of flexion from full extension to full flexion.
Figures 8E, 9, 10, 11, 12:
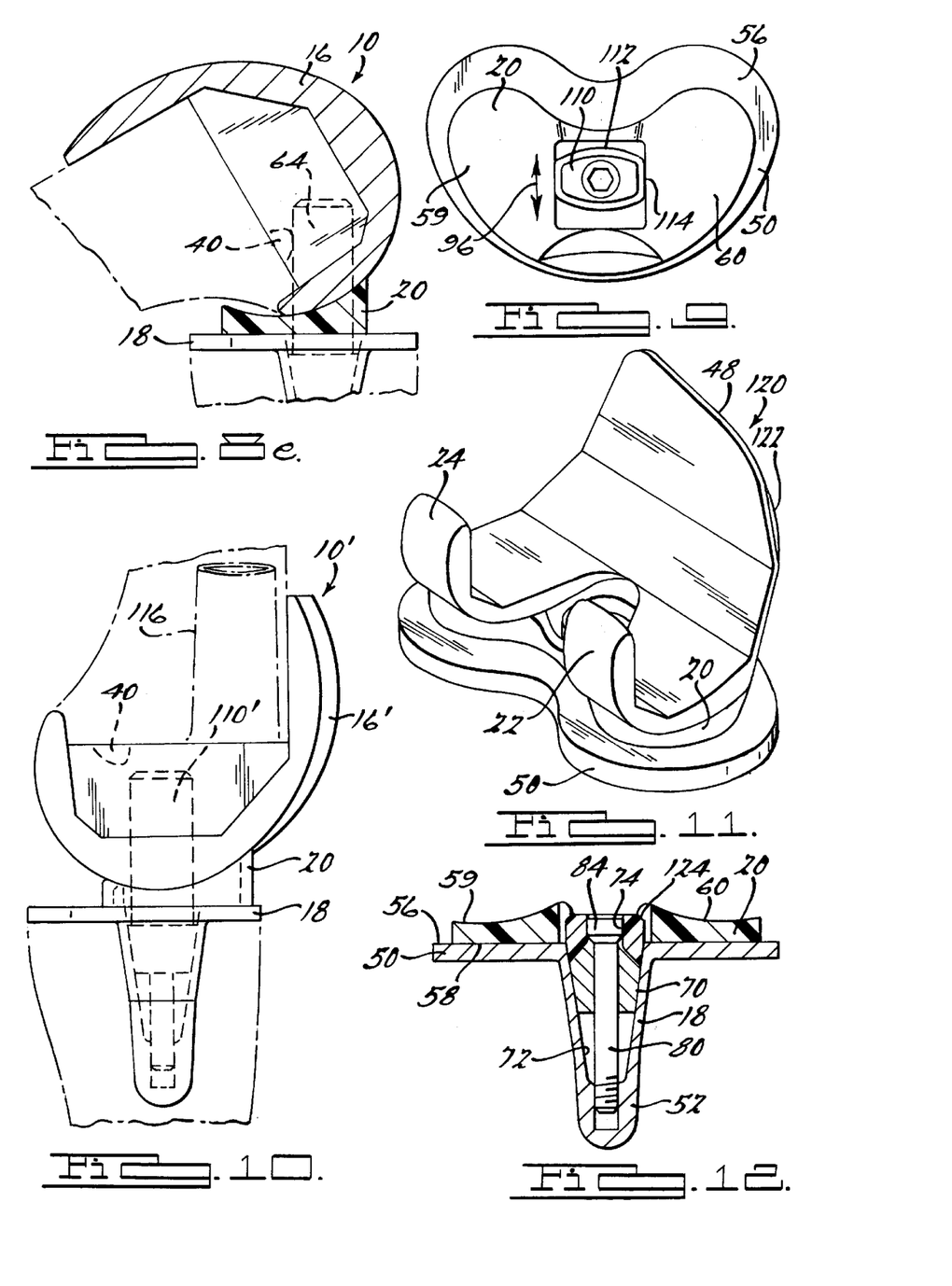
FIG. 9 is a top view of an assembled tibial component and bearing component of a fully constrained knee joint prosthesis according to the teachings of a second preferred embodiment of the present invention.
FIG. 10 is a sagittal elevational view of the fully constrained knee joint prosthesis of FIG. 9 with the tibia and the femur of the natural knee shown in phantom.
FIG. 11 is a perspective view of a primary knee joint prosthesis according to the teachings of a third preferred embodiment of the present invention.
FIG. 12 is a coronal sectional view of the tibial component and bearing member of the primary knee joint prosthesis of FIG. 11.

Turning to FIGS. 8a–8e, partial sagittal sectional views of the posterior stabilized (PS) knee joint prosthesis 10 illustrating the movement of the femoral component 16 and the floating bearing 20 relative to the tibial component 18 are shown from full extension in FIG. 8a to full flexion in FIG. 8e. In FIG. 8a, the posterior stabilized (PS) knee joint prosthesis 10, both anteriorly and posteriorly, is inherently stable at full extension when the patient is standing. In this position, the first and second femoral bearing surfaces 26 and 28 are rested within the first and second tibial bearing surfaces 59 and 60 of the floating bearing 20, respectively. The anterior surface 102 and the posterior surface 104 of the post 64 do not engage the anterior portion 106 or the posterior portion 108 of the sidewall 66. The posterior surface 104 of the post 64 further does not engage the engagement member 40 of the femoral component 16. If the knee joint prosthesis 10 would undergo a large hyperextension or forward rollback (approximately 10°), the anterior surface 102 of the post 64 would engage the anterior portion 38 of box 42 in the femoral component 16, while the floating bearing 20 would generally slide posteriorly relative to the tibial tray 50. This engagement will further avoid posterior dislocation of the femoral component 16 relative to the tibial component 18.

The femoral component 16 with respect to the tibial component 18 and the floating bearing 20 is generally most unrestricted between full extension, as illustrated in FIG. 8a and the point of flexion where the posterior engagement member 40 and the posterior surface 104 of the post 64 initially engage, as illustrated in FIG. 8b. This engagement generally occurs between about 20° to 45° of flexion. Within this range between 0° to about 20° to 45°, the femoral component 16 is permitted to translate in the sagittal plane along with the floating bearing 20 relative to the tibial component 18. In particular, the femoral component 16 will remain substantially congruently positioned relative to the floating bearing 20 to provide a full articulating contact surface during this range of flexion. In other words, the femoral component 16 and the floating bearing 20 are both able to move anteriorly and posteriorly relatively freely with respect to the tibial component 18, via the bearing surfaces 56 and 58 between the floating bearing 20 and the tibial tray 50. However, it should be further understood that the exact amount of translation in the sagittal plane permitted by the knee joint prosthesis 10 will of course, vary depending on the forces imparted by local soft tissues, muscles, tendons, ligaments, as well as forces transmitted from the tibia and fibula. These forces will, of course, vary from patient to patient, from activity to activity, as well as from implantation to implantation.

When flexion exceeds approximately 20° to 45°, as shown in FIG. 8c, the posterior engagement member 40 of the femoral component 16 engages the posterior surface 104 of the post 64. This engagement forces rollback of the floating bearing 20 posteriorly relative to the tibial tray 50, whereby the floating bearing 20 having bearing surface 58 slides relative to bearing surface 56 of tibial tray 50. While this forced rollback of the floating bearing 20 is occurring, the bearing surfaces 26 and 28 of the first and second condyles 24 and 26 are fully nestingly received within the bearing surfaces 59 and 60 of the floating bearing 20. This forced rollback of the floating bearing 20 creates the desired femoral rollback of an anatomical knee joint. As flexion continues from about 60° shown in FIG. 8c to about 110° shown in FIG. 8e, a forced rollback of the floating bearing 20 relative to the tibial tray 50 continues to occur, while a full surface contact area between the first and second condyles 22 and 24 and the floating bearing 20 are maintained, via cooperating surfaces 26, 28 and 59, 60, respectively.

As can be observed from FIGS. 8a–8e, the forced rollback provided by the engagement of the fixed modular post 64 with the engagement member 40 enables a full surface contact area to be maintained between the femoral component 16 and the floating bearing 20. This full surface contact is achieved because rollback is occurring between the floating bearing 20 and the tibial component 18, via a sliding of the floating bearing 20 posteriorly atop the tibial tray 50 with surfaces 56 and 58. This is in contrast to existing fixed bearing knee prostheses which achieve rollback, via the translation of the femoral component relative to a fixed bearing atop the tibial component. With conventional floating bearing knee prostheses, these devices either do not provide any type of guide post secured to the tibia and simply rely on soft tissue to produce the rollback or they utilize a post which is integral with the floating bearing. Accordingly, the rollback in the prior art is again occurring between the femoral component 16 and the floating bearing 20, as opposed to the floating bearing 20 and the tibial component 18, which provides a substantially increased surface area during rollback for overall reduced wear of the bearing member 20.

Turning to FIG. 9, a top view of the tibial component 18 and the floating bearing 20 is shown with a fully constrained guide post 110. In this regard, the post 110 is substantially similar to the post 64, except that the outer peripheral wall 112 is shaped with truncated ends 114. In this regard, the endwalls 114 slidably engage the sidewalls 66 of opening 62, thereby eliminating any lateral or medial movement 98 or rotational movement 100 with respect to the tibial component 18. This fully constrained type knee therefore, only allows anterior and posterior movement 96 of the floating bearing 20 relative to the tibial component 18. Thus, by simply replacing the post 64 with a new post 110, the knee joint prosthesis 10 may be converted from a posterior stabilized (PS) knee joint prosthesis 10 to a fully constrained knee joint prosthesis 10'. This provides for a fully constrained knee that maintains the large contact area (i.e. >300 mm$^2$), as well as having the desired rollback. It should further be noted that by simply changing the shape of the post 64, cam member 40, or the opening 62 in the bearing 20, the anterior motion may be adjusted. Moreover, removable sleeves may be fashioned that slide on to post 64 to provide for further adjustment.

This convertability enables a substantially convenient method for changing from a posterior stabilized (PS) to a fully constrained knee joint by simply replacing the guide post 64, via the threaded bolt 80. Should further stability be required with the femoral component 16, a closed box femoral component 16' may be used which includes a femoral stem 116. In this situation, the original femoral component 16 would be replaced with the new femoral component 16', while the tibial component 18 and the bearing component 20 would stay the same. It should further be noted that the movement of the femoral component 16, the tibial component 18 and bearing member 20 relative to one another along the sagittal plane is substantially similar to that shown in FIGS. 8a–8e of the posterior stabilized (PS) knee joint prosthesis 10.

Turning to FIGS. 11 and 12, a primary knee joint prosthesis 120 according to the teachings of a third preferred embodiment of the present invention is shown. In this regard, the tibial component 18 and the floating bearing 20 are substantially the same as used with the other preferred embodiments. The only differences are with respect to the femoral component 122 and the central post 124. In this regard, the post 124 is substantially similar to the post 64 except that the height of the post is reduced so that it does not extend above or out beyond the opening 62. The femoral component 122 includes the first and second condyles 22 and 24 having the first and second bearing surfaces 26 and 28, respectively. The femoral component 122 further includes the articulating patella portion 48. What is essentially missing is the box 42 which provides the posterior engagement member 40. Because of this, there is no mechanical engagement of the post 124 relative to the femoral component 122 to force a rollback of the floating bearing 20 relative to the tibial component 18.

The rollback of the floating bearing 20 is achieved by the remaining soft tissues and ligaments of the patient. In this regard, the floating bearing 20 is initially centrally positioned about the tibial tray 50 similar to the other preferred embodiments during full extension. At about 25° to 45° of flexion, rollback of the floating bearing 20 starts and is substantially maintained through full flexion because of the cruciate ligament causing the floating bearing 20 to roll back. Here again, the primary knee joint prosthesis 120 may be converted from a primary knee joint prosthesis 120 to a posterior stabilized (PS) knee joint prosthesis 10 or a fully constrained knee joint prosthesis 10' by simply replacing the post 124 and the femoral component 122 without having to change the tibial component 18 or the tibial bearing 20.

Figure 13:
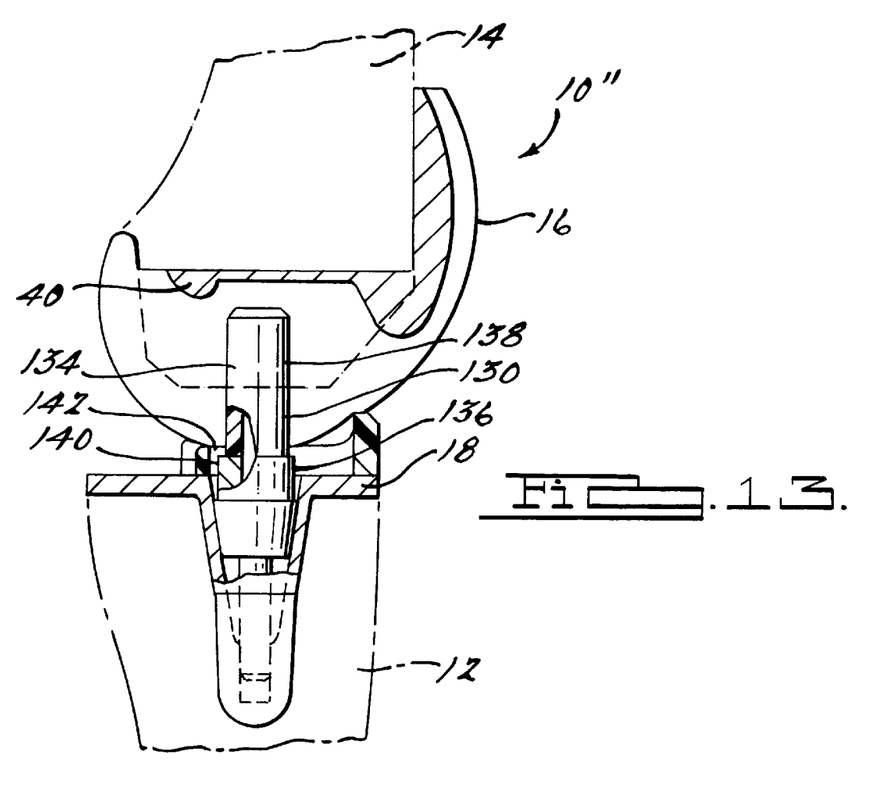
FIG. 13 is a partial sagittal sectional view of a posterior stabilized (PS) knee joint prosthesis according to the teachings of a fourth preferred embodiment of the present invention.

Turning to FIG. 13, a partial sagittal sectional view of a posterior stabilized (PS) knee joint prosthesis 10" according to the teachings of a fourth preferred embodiment of the present invention is shown. In this regard, like reference numerals will be used to identify like structures with respect to the knee joint prosthesis 10. In this regard, the only differences are with respect to the shape of the guide post 130 and the floating bearing 132. The guide post 130 is secured to the tibial component 18 in substantially the same manner as that shown with regard to the knee joint prosthesis 10. The difference in the guide post 130 is that it includes a first guide portion 134 and a second guide portion 136. The first guide portion 134 is defined by a substantially oval shaped sidewall 138 similar to that shown in FIG. 2. The second guide portion 136 is also formed by an oval shaped sidewall 140 which is larger than the shaped sidewall 138. The first guide portion 134 is preferably formed from a molded polymer, such as UHMWPE and the second guide portion 136 is preferably formed from a cobalt—chromium—molybdenum. However, various other combinations between the first guide portion 134 and the second guide portion 136 can also be provided such as a complete polymer assembly, complete metallic assembly or any other combination.

The second guide portion 136 has a height which does not extend beyond the bearing 134 and is positioned within opening 142 such that the second guide portion 136 only engages and controls the movement of the floating bearing 132 relative to the tibial component 18. The second guide portion 134 extends into the box 42 of the femoral component 16 such that the second guide portion 134 is operable to be engaged by the cam member 40 to control the movement of the femoral component 16 relative to the bearing 132. In other words, the two stage guide post 138 individually controls the relative movement of the femoral component 16 and the bearing component 132 with the first guide portion 134 and the second guide portion 136, respectively. This provides for increased adjustability in the relative articulating motion of the knee joint prosthesis 10" while further maintaining a substantially full and continuous contact area between the femoral component 16 and the floating bearing 132 from extension to full flexion.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A knee joint prosthesis for replacing the articulating knee portion of a femur and a tibia, said knee joint prosthesis comprising:

a femoral component having an engagement member, a first femoral bearing surface and a second femoral bearing surface;

a tibial component having a tibial bearing surface;

a bearing member having a first bearing surface operable to articulate with said first femoral bearing surface, a second bearing surface operable to articulate with said second femoral bearing surface, and a third bearing surface operable to articulate with said tibial bearing surface;

a first removable guide post extending from said tibial component, said first removable guide post operable to be engaged by said engagement member of said femoral component, said first removable guide post includes a first guide portion having a first shape and a second guide portion having a second shape, said first shape being different from said second shape, said first guide portion operable to control movement of said femoral component and said second guide portion operable to control movement of said bearing member; and a second removable guide post, wherein upon replacing said first removable guide post with said second removable guide post, said knee joint prosthesis is converted from a first type knee joint prosthesis to a second type knee joint prosthesis with each said prosthesis having a different type of constraint.

2. The knee joint prosthesis as defined in claim 1 wherein said engagement member of said femoral component is a cam member.

3. The knee joint prosthesis as defined in claim 1 wherein said tibial bearing surface is a substantially planar polished surface.

4. The knee joint prosthesis as defined in claim 1 wherein said bearing member defines an opening passing therethrough and at least one of said first and second removable guide posts is operable to extend through said opening in said bearing member.

5. The knee joint prosthesis as defined in claim 1 wherein at least one of said first and second removable guide posts is operable to be removably secured to said tibial component, via a Morse type taper.

6. The knee joint prosthesis as defined in claim 1 wherein said first removable guide post has a substantially oval shaped outer sidewall along at least one of said first guide portion and said second guide portion.

7. The knee joint prosthesis as defined in claim 6 wherein said substantially oval shaped out sidewall of said first removable guide post has truncated ends.

8. The knee joint prosthesis as defined in claim 1 wherein said first femoral bearing surface articulating with said first bearing surface and said second femoral bearing surface articulating with said second bearing surface provides a contact area of greater than about 300 mm$^2$ from extension to full flexion.

9. The knee joint prosthesis as defined in claim 1 wherein upon said engagement member engaging one of said first and second removable guide posts, said femoral component prevents said bearing member from moving substantially anteriorly.

10. The knee joint prosthesis as defined in claim 1 wherein upon said engagement member engaging one of said first and second removable guide posts, said femoral component forces the bearing member to move posteriorly relative to said tibial component.

11. A knee joint prosthesis for replacing the articulating knee portion of a femur and a tibia, said knee joint prosthesis comprising:

a femoral component having at least one femoral bearing surface;

a tibial component having at least one tibial bearing surface;

a bearing member having a first bearing surface operable to articulate with said at least one femoral bearing surface and a second bearing surface operable to articulate with said at least one tibial bearing surface;

a first removable guide post operable to be removably coupled to said tibial component, said first removable guide post operable to be engaged by said femoral component; and a second removable guide post operable to be removably coupled to said tibial component, said second removable guide post operable to be engaged by said femoral component, wherein upon selection of one of said first and second removable guide posts changes the type of constraint exhibited by the knee joint prosthesis whereby upon engagement of said femoral component with one of said first and second removable guide posts, said femoral component controls at least a portion of the movement of said bearing member relative to said tibial component.

12. The knee joint prosthesis as defined in claim 11 wherein said femoral component further includes a cam member operable to engage one of said first and second removable guide posts during flexion of said knee joint prosthesis.

13. The knee joint prosthesis as defined in claim 11 wherein said bearing member defines an opening passing therethrough and at least one of said first and second removable guide posts extends through said opening in said bearing member.

14. The knee joint prosthesis as defined in claim 11 wherein said femoral bearing surface is formed by a condyle portion defined by a first anterior radius and a smaller posterior radius extending along a sagittal plane, said smaller posterior radius extending anterior said first bearing surface of said bearing member.

15. The knee joint prosthesis as defined in claim 11 wherein said first bearing surface of said bearing member is defined by a single radius along a sagittal plane.

16. The knee joint prosthesis as defined in claim 15 wherein said first bearing surface is defined by a second radius along a coronal plane.

17. A knee joint prosthesis system for replacing the articulating knee portion of a femur and a tibia, said knee joint prosthesis system comprising:

a first femoral component having at least a first femoral bearing surface;

a tibial component having at least one tibial bearing surface;

a bearing member having a first bearing surface operable to articulate with said first femoral bearing surface and a second bearing surface operable to articulate with said at least one tibial bearing surface; and a plurality of removable guide posts, each of said removable guide posts operable to be removably coupled to said tibial component and be engaged by said first femoral component, at least one of said removable guide posts includes a first guide portion having a first shape and a second guide portion having a second shape, said first shape being different from said second shape, said first guide portion operable to control movement of said femoral component and said second guide portion operable to control movement of said bearing member, wherein selection of one of said removable guide posts changes the type of constraint exhibited by the femoral knee joint prosthesis system.

18. The knee joint prosthesis system as defined in claim 17 further comprising a second femoral component, said first femoral component is a primary femoral component and said second femoral component is a posterior stabilized femoral component.

19. The knee joint prosthesis system as defined in claim 17 wherein said plurality of removable guide posts includes a first guide post which is operable to enable anterior to posterior, medial to lateral, and rotational movement of said bearing member relative to said tibial component, and a second guide post operable to enable anterior to posterior movement of said bearing member relative to said tibial component.

20. The knee joint prosthesis system as defined in claim 17 wherein one of said removable guide posts is operable to be engaged by said first femoral component, whereby said femoral component forces said bearing member to move posteriorly relative to said tibial component.

* * * * *

UNITED STATES PATENT AND TRADEMARK OFFICE
CERTIFICATE OF CORRECTION

PATENT NO. : 6,165,223
DATED : December 26, 2000
INVENTOR(S) : Robert Metzger, David Ray Brown, Troy Hershberger and Kevin Cox It is certified that error appears in the above-identified patent and that said Letters Patent is hereby corrected as shown below:

<u>Title page,</u>
Under OTHER PUBLICATIONS, "Joine" should be -- Joint --
"Lawrency" should be -- Lawrence --

<u>Column 8,</u>
Line 64, after "112 is" insert -- oval --

<u>Column 10,</u>
Line 9, after "larger than the" insert -- oval --

Signed and Sealed this

Sixteenth Day of July, 2002

*Attest:*

JAMES E. ROGAN
*Attesting Officer*  *Director of the United States Patent and Trademark Office*